Figure 1:
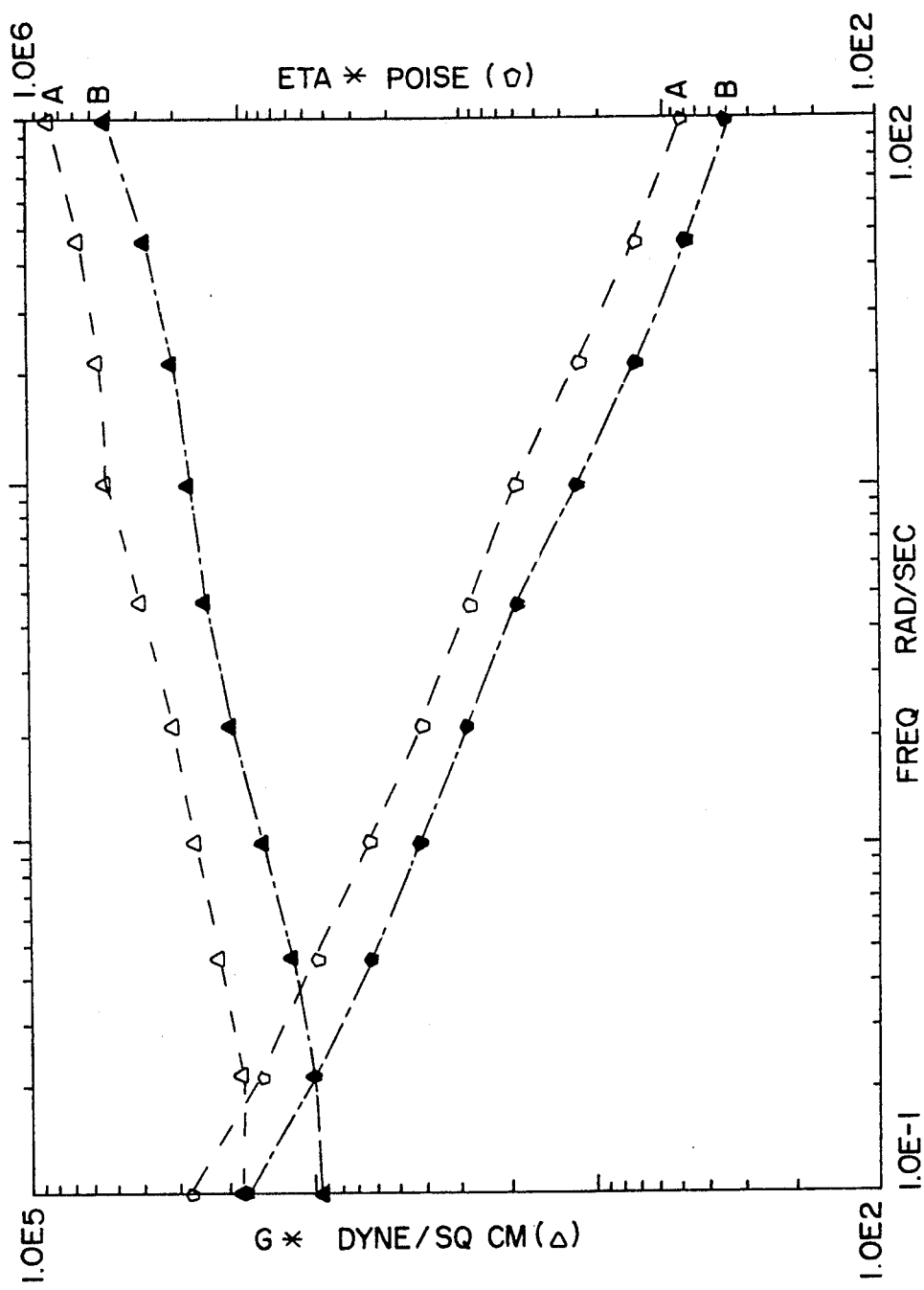

United States Patent [19]
Prosise

[11] Patent Number: 5,286,764
[45] Date of Patent: Feb. 15, 1994

[54] HIGH LOAD POLYMER PASTES AS A DENTURE ADHESIVE

[75] Inventor: William E. Prosise, Ramsey, N.J.

[73] Assignee: ISP Investments Inc., Wilmington, Del.

[21] Appl. No.: 916,448

[22] Filed: Jul. 20, 1992

[51] Int. Cl.$^5$ .......................... A61K 6/00; A61C 13/12
[52] U.S. Cl. .................................. 523/120; 433/168.1; 433/180; 524/312; 524/318
[58] Field of Search ............... 523/120; 524/308, 312, 524/318; 433/168.1, 180

[56] References Cited

U.S. PATENT DOCUMENTS

| | | |
|---|---|---|
| 3,868,340 | 2/1975 | Keegan et al. ...................... 523/120 |
| 4,542,168 | 9/1985 | Chang et al. ........................ 523/120 |
| 4,804,412 | 2/1989 | Komiyama et al. ................. 523/120 |
| 5,055,046 | 10/1991 | Chaudhuri et al. ................. 523/120 |

Primary Examiner—Paul R. Michl
Assistant Examiner—LaVonda DeWitt
Attorney, Agent, or Firm—Marilyn J. Maue; Joshua J. Ward

[57] ABSTRACT

This invention relates to a process of preparing a high polymer load dispersion of an innocuous adhesive polymeric resin in an oil base containing between 0.01 and about 5 wt. % of a non-toxic, food grade surfactant and to coating and affixing a denture material coated with said adhesive to the gums for increased strength and extended holding power.

11 Claims, 3 Drawing Sheets

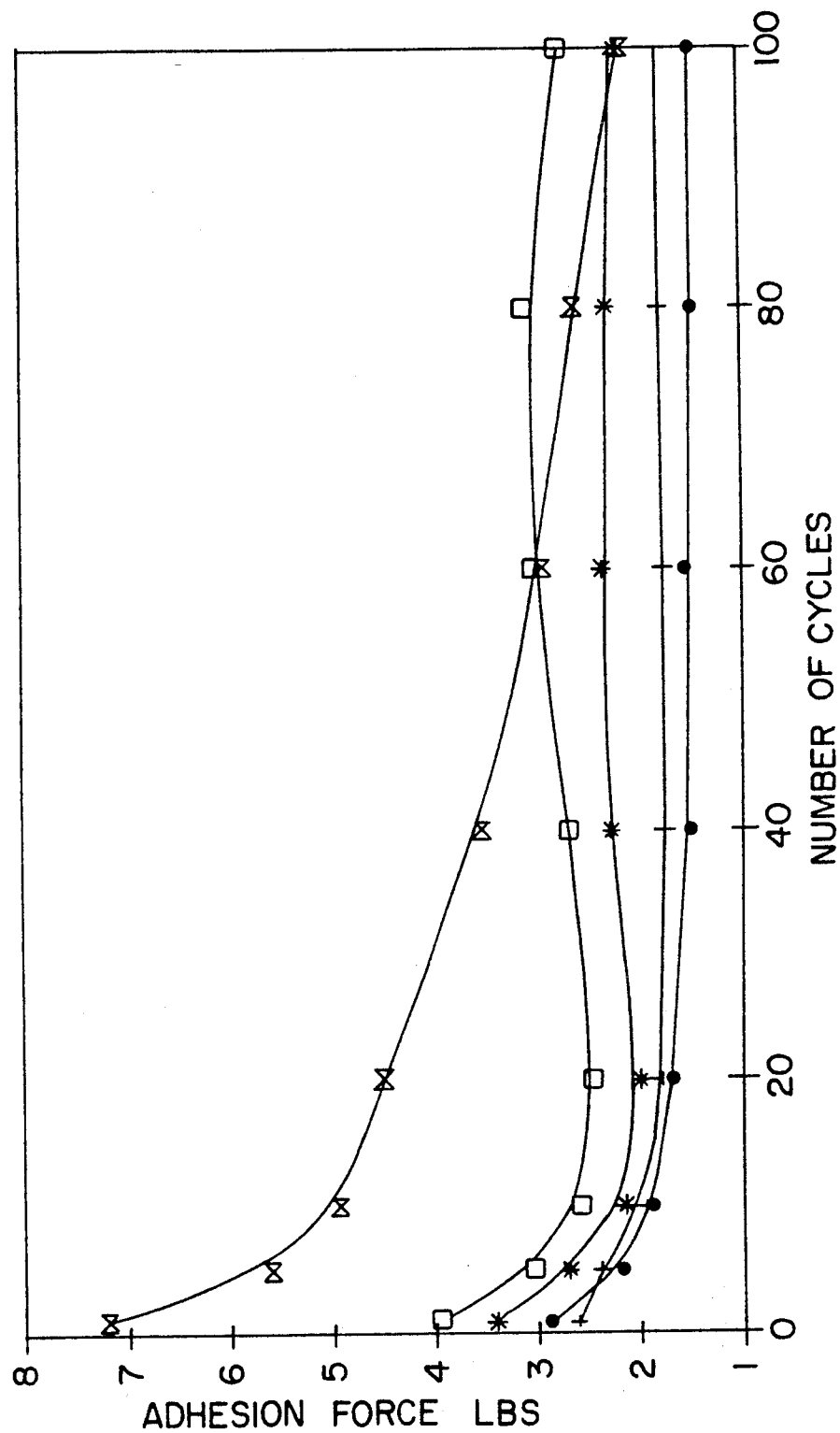

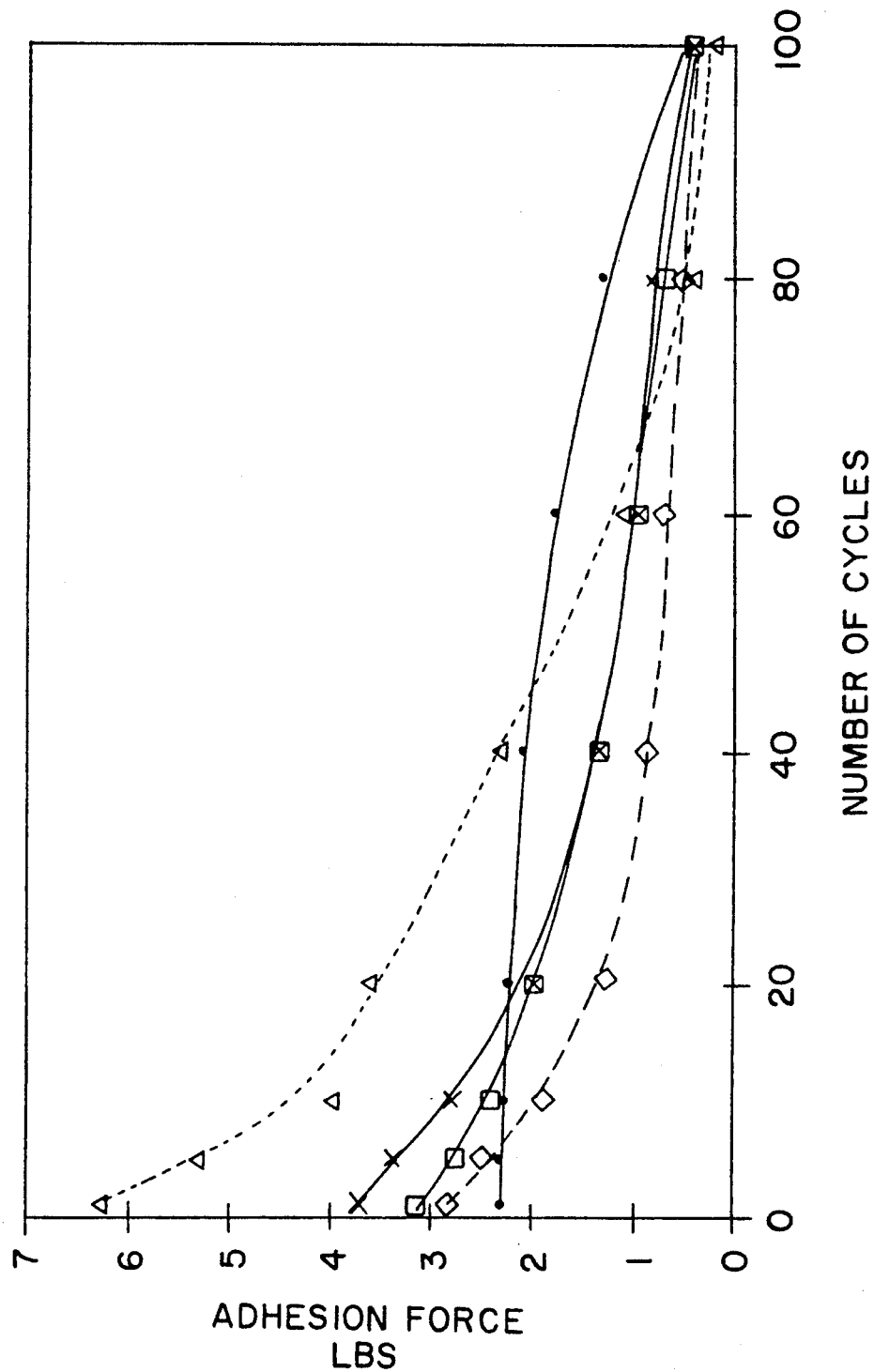

HIGH LOAD POLYMER PASTES AS A DENTURE ADHESIVE

In one aspect this invention relates to the preparation and use of a denture adhesive composition which contains high concentrations of an adhesive polymeric resin for added holding power while retaining a soft paste or gel-like consistency for easy pressure evacuation from a tube or flexible container. In another aspect, the invention relates to the use of the highly moldable, non-sensitizing denture adhesive containing a viscosity limiting agent.

BACKGROUND OF THE INVENTION

Various denture adhesive compositions using polymers are described in the patent literature, for example see U.S. Pat. Nos. 5,037,924; 4,910,247; 4,318,742 and 4,393,080. Generally such compositions exhibit resistance to biological fluids, are non-irritating and have good adhesion over a limited period of time. However, it is generally desired to increase the resin content of the existing formulations to reinforce and extend the adhesive holding power while still retaining a viscosity which permits high conformity to the shape of the mucous membrane to which the adhesive is applied. Attempts to formulate compositions of smooth paste or gel-like consistency which contain up to 45 or 65% solids have not met with success since increase in resin content is invariably accompanied by an undesired increase in viscosity such that the paste-like and structure conforming properties are greatly diminished.

Accordingly, it is an object of this invention to overcome the above difficulties while still retaining the desirable properties of prior denture adhesives.

Another object of the invention is to provide a process for introducing a viscosity limiting compound into commercial denture adhesive formulations which permits marked increase in polymer loading with minimal increase in composition viscosity.

Still another object is to provide a process of using a denture adhesive which is simple and economical to prepare.

These and other objects will become apparent from the following description and disclosure.

THE INVENTION

This invention concerns the incorporation of certain innocuous surfactants in a polymeric denture adhesive aqueous suspension or dispersion to control the viscosity of the adhesive and to maintain a paste or gel-like consistency while permitting considerable increase in the polymeric resin concentration for additional strength and lasting holding power.

This discovery is indeed surprising since surfactants are known release agents and, as such would not be expected to improve denture adhesion. However, it is now discovered that when the surfactant is employed in a critically small amount, it functions as a low level dispersant and exhibits none of its potential release properties in the denture formulation. Thus, in accordance with this invention between 0.01 and 5 wt. % of a hydrolyzable, food grade surfactant is incorporated into a denture adhesive formulation containing an innocuous polymeric resin to provide a composition having a reduced oil carrier phase and a significantly higher polymer concentration resulting in extended holding power and stable adhesion viscosity.

The food grade surfactants represented for this invention include any non-toxic surfactant having a low HLB (hydrophilic/lipophilic balance), examples of which are mono- and/or di- glycerides, polyglycerol esters such as glycerol monostearate (GMS-90), triglycerol monostearate (SANTONE 3-1-S), octaglycerol monooleate (SANTONE 8-1-0), triglycerol mixed with fatty acid esters (SANTONE 3-1-SH), certain ester salts, e.g. an alkali metal salt such as calcium or potassium stearoyl lactate (e.g. VERV Ca), a succinylated or ethoxylated mono- or di- glyceride, a polyoxyethylene ether of a fatty acid ester of sorbitol anhydride and any of the hydrolyzable phospholipids or their mixtures described in copending U.S. patent application Ser. No. FDN-1952, entitled HIGH LOAD POLYMER PASTES AS PHARMACEUTICAL ADHESIVES, filed concurrently herewith for William E. Prosise and Ki-Ho Chung. Lecithins, as defined in the Official Monograph of the United States Pharmacopeia, National Formulary XVII, employed individually or in admixture, are particularly suitable viscosity controlling agents for this invention. Examples of commercially available lecithin mixtures include CENTROLEX-F, OVATHIN, and the like.

The present surfactant or an admixture thereof is added to the adhesive formulation in a critical amount of between 0.01 and 5 wt. %; preferably in an amount between about 0.05 and about 1 wt. %, based on the total adhesive composition. The concentration of the surfactant or surfactant mixture with respect to the polymer is between about 0.02 and about 10 wt. %, preferably between about 0.1 and about 2 wt. %. When added within the above critical ranges, the surfactant exhibits none of its release properties and instead increases the polymer load potential by between about 3 and about 15% without raising the viscosity of the mixture. Thus, a stronger, time extended adhesive which resists deterioration by action of saliva and moisture is achieved. It has been found that the present surfactant containing compositions can be obtained with up to 70% solids in the form of a gel or soft pasty product.

The polymeric resins employed in the dental adhesives of the invention are any of those commercially available polymeric dental adhesives and include blends or mixtures of mixed or partial salts of maleic anhydride/acrylic copolymers, vinyl ether/maleic acid copolymers, vinyl ether/maleic acid/maleic anhydride terpolymers and or alkyl amino salts thereof, maleic anhydride/vinyl ether/isobutylene terpolymers, vinyl ether/maleic anhydride copolymer with hydroxylated compounds such as a polyethoxylated fatty alcohol, oleyl alcohol, nonyl phenol, octyl phenol, polyethylene glycol, propylene glycol and similar compounds and mixed salts of vinyl ether/maleic anhydride and stearic acid and the like, examples of which are to be found in U.S. Pat. Nos. 5,104,926, filed Dec. 22, 1989; 5,066,709, filed Sep. 20, 1990 and Ser. No. 786,638, filed Nov. 1, 1991, as well as in the U.S. Pat. Nos. referred to above in the discussion on the Background of the Invention.

The above polymeric resins are generally dispersed in a non-toxic oil base, such as white petrolatum, mineral oil, polyethylene wax, a microcrystalline wax, petroleum jelly, beeswax, benzoated lard, glycerine, whey, polyethylene or polypropylene glycols, zinc oxide eugenol paste, and the like. The weight ratio of oil base to polymer previously employed was within the range of from about 5:1 to about 1:2. By incorporation of the present surfactant, this ratio can be reduced to 1:5 oil to polymer depending on the amount of surfactant added and the desired thickness of the composition.

The denture adhesive composition may also contain various acjuvants such as flavoring agents, coloring agents, emulsifiers, thickeners, as well as innocuous preservatives such as hexamethylene tetramine, an alkyl or aryl ester of p-hydroxybenzoic acid, etc. which additives are incorporated in minor amounts, as described in the art. Also the composition may contain a humectant to assist moisture absorption of the adhesive dispersion. The present compositions are substantially anhydrous, although up to 10 wt. % water can be tolerated without detriment.

Representative of a useful commercial adhesive formulation to which the present surfactants are added is the following.

|  | wt. % |
|---|---|
| Light mineral oil | 8-15 |
| White petrolatum | 20-25 |
| Natural gum or wax | 20-40 |
| Emulsifier | 0.5-1 |
| Polymer resin | 20-30 |
| Flavoring Agent | QS |
| Coloring Agent | QS |

The manner in which the present compositions may be prepared is both economical and commercially feasible. Generally, the present compositions are prepared by adding the viscosity controlling surfactant to a melt of the oil base optionally containing other liquid adjuvants, such as coloring and/or flavoring agents. The melt is usually obtained at a temperature of from about 85° C. to about 200° C. and forms a liquid portion of the composition. Solid polymer resin and any thickening component which may be desired is separately dry blended to a uniform consistency, and is then added to the melt under agitation to form a uniform dispersion. Constant agitation is continued during cooling of the resulting dispersion so as to maintain the uniform distribution of the polymer in the surfactant/oil base. The mixing of solids with the melt is conducted at a temperature of between about 50° C. and about 180° C., preferably between about 70° C. and about 100° C. for a period of from about 8 minutes to about 5 hours or until a uniform smooth gel or paste consistency is achieved.

The resulting mixture is a substantially anhydrous paste or gel ready for use which is easily extracted from a tube or other container in which it may be packaged and is applied in an effective adhesive amount to a denture, usually in a thickness of from about 0.5 to about 15 mils thickness for lasting holding power.

Having thus generally described the invention, reference is now had to the following which illustrate preferred embodiments and comparative tests by way of examples but which are not to be construed as limiting to the scope of this invention as more broadly set forth above and in the appended claims.

EXAMPLES 1-16

The following compositions in Table I were prepared by forming a melt of mineral oil, white petrolatum, and lipoid emulsifier in a jacketed Hobart Mixer equipped with a paddle stirrer operating at about 300 rpm. Coloring and flavoring agents were then added to the melt and mixed therein until a uniform composition was achieved, usually within a period of from about 10 to 30 minutes.

Separately, the cellulose thickener and Gantrez MS-955D* were dry blended in a Paterson-Kelly V blender until a uniform composition was obtained, within a period of 10-15 minutes at about 80°-85° C., after which the dry blended mixture was gradually added to the melt over a period of 30 minutes under constant agitation at a temperature of about 70-75° C. so as to obtain a uniform dispersion of solids in the melt. The resulting dispersion was then cooled to room temperature with cooling water under constant agitation. These compositions are reported in following Table I.

* Mixed Na and Ca salts of poly(methyl vinyl ether/maleic anhydride having a molecular weight of 600,000-1,500,000

TABLE I

| Composition | WEIGHT % | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Light Mineral Oil | 11.90 | 12.15 | 12.28 | 12.34 | 12.40 | 18.90 | 19.15 | 18.90 | 19.15 | 19.40 | 18.90 | 19.15 | 18.90 | 19.15 | 18.90 | 18.90 |
| White Petrolatum | 23.60 | 23.60 | 23.60 | 23.60 | 23.60 | 30.40 | 30.40 | 30.40 | 30.40 | 30.40 | 30.40 | 30.40 | 30.40 | 30.40 | 30.40 | 30.40 |
| Emulsifier | | | | | | | | | | | | | | | | |
| polyglycerol ester[3] | — | — | — | — | — | 0.50 | 0.25 | — | — | — | — | — | — | — | — | — |
| octaglycerol mono-oleate (SANTONE 3-1-S) | — | — | — | — | — | — | — | — | — | — | — | — | — | — | 0.50 | — |
| glycerol mono-stearate (GMS-90)[1] | — | — | — | — | — | — | — | 0.50 | 0.25 | — | — | — | — | — | — | — |
| calcium stearoyl lactylate (VERV Ca)[2] | — | — | — | — | — | — | — | — | — | — | 0.50 | 0.25 | — | — | — | — |
| Lecithin[4] | 0.50 | 0.25 | 0.13 | 0.06 | — | — | — | — | — | — | — | — | 0.50 | 0.25 | — | — |
| Gantrez MS-995D | 26.00 | 26.00 | 26.00 | 26.00 | 26.00 | 26.00 | 26.00 | 26.00 | 26.00 | 26.00 | 26.00 | 26.00 | 26.00 | 26.00 | — | — |
| CENTROLEX F | — | — | — | — | — | — | — | — | — | — | — | — | — | — | — | 0.50 |
| Cellulose thickener | | | | | | | | | | | | | | | | |
| hydroxypropylmethyl cellulose | 38.00 | 38.00 | 38.00 | 38.00 | 38.00 | — | — | — | — | — | — | — | — | — | — | — |
| carboyxmethyl cellulose | — | — | — | — | — | 24.20 | 24.20 | 24.20 | 24.20 | 24.20 | 24.20 | 24.20 | 24.20 | 24.20 | 24.20 | 24.20 |
| Color and flavoring agents | QS | QS | QS | QS | QS | QS | QS | QS | QS | QS | QS | QS | QS | QS | QS | QS |

[1]supplied by Bredda Corp.
[2]supplied by Patco Corp.
[3]supplied by Durkee Foods
[4]CENTROLEX ® F supplied by Central Saya Co.

The above compositions were then evaluated for Tube Squeezability, i.e. a viscosity determination and for adhesion strength and results are reported in following Table II.

TUBE SQUEEZE TEST

The squeezable tube test was carried out as described by B. Noren in the Journal of the Society of Cosmetic Chemistry Volume 27, pages 47-61, 1976, entitled A METHOD TO EVALUATE THE TUBE SQUEEZING PROPERTIES OF TOOTHPASTE. Specifically, this test method comprises taking a 40 g. sample of the composition and filling a 1 inch diameter GLAMINATE ® tube (American National Can Corp.) having a 0.39 inch length and having a 0.168 inch diameter orifice. Then pressing the tube with a 1 inch circular piston exerting 20 psig for exactly 5.000 seconds. The grams of extruded sample were measured and recorded as shown in TABLE II.

INSTRON STUDIES FOR ADHESION

A small amount (~2 g.) of denture adhesive is subjected to cyclic compressive and tensile stresses between two polymethylmethacrylate plates.

The first step in running this test is to bring the plates together to obtain the zero position (A). The upper plate is then raised 0.06 inch and the upper cycle limit on the Instron is set at this point (B). The upper plate is then lowered and the lower cycle limit is set (C). In its lowest position, then, the upper plate is 0.03 inch from the lower plate.

With these Instron settings determined, the upper plate was then raised high enough to spread 2 grams of sample uniformly over the top of the lower plate.. Then 200 ml of simulated salivary fluid was added so that the sample was barely covered. The Instron crosshead was cycled between the set limits at a crosshead speed of 0.2 in./min. The Instron chart was set in the continuous mode at a speed of 2 in./min. to record the compression and adhesion force for each cycle up to 100 cycles.

At the end of 100 cycles, the upper plate motion was halted and the plate cleaned. The apparatus was thoroughly washed and dried in preparation for the next denture adhesive evaluation.

The saliva solution was changed for each denture adhesive. Each recording was analyzed and the adhesional forces (lbs.) for the 1st, 5th, 10th, 15th . . . 100th cycles were recorded.

TABLE II

| Composition | Squeezability (g)[(1)] | Adhesion Strength lbs. at 100 cycles |
|---|---|---|
| 1 | 10.9 | 1.5 |
| 2 | 10.8 | 1.75 |
| 3 | 8.3 | 2.3 |
| 4 | 8.8 | 2.8 |
| 5 | 3.4* | 2.2 |
| 6 | 14.0 | 0.5 |
| 7 | 14.0 | 0.5 |
| 8 | 13.0 | 0.5 |
| 9 | 12.0 | 0.3 |
| 10 | 6.0 | 0.1 |
| 11 | 15.0 | 0.4 |
| 12 | 14.5 | 0.2 |
| 13 | 15.8 | 0.4 |
| 14 | 15.6 | 0.4 |

*composition too thick - not squeezable
[(1)]grams of product squeezed from tube

RHEOLOGICAL CHARACTERIZATION

The dynamic rheological profile of the following adhesive methyl vinyl ether/maleic acid sodium and calcium salt compositions were compared and plotted on a log graph represented by FIG. I.

|  | COMPOSITION A* | COMPOSITION B** |
|---|---|---|
| Ca/Na salt of MVE/MA | 33.333 wt % | 33.333 wt % |
| white petrolatum | 66.667 wt % | 66.667 wt % |
| CENTROLEX-F | — | 0.5 wt % |

*represented by broken line - - - -
**represented by broken line — - — - — -

* represented by broken line - - -
** represented by broken line

In FIG. I, G represents the complex modulus, ETA represents the complex viscosity against the X axis angular frequency.

Dynamic measurements were performed at room temperature (25±1° C.) to characterize the rheological properties of denture adhesive model systems. Rheometries Mechanical Spectrometer 800 with two 25 mm diameter parallel plates was used for the measurements.

In dynamic measurement, an oscillatory strain (sinusoidal strain) was applied on the sample and the response stress was measured, while in steady measurement one directional shear strain was applied on the sample and the response stress was measured. The dynamic measurements has many advantages: it is easy to run from low frequency to high frequency (wide range of time scale) and it does not destroy structure in the material because it applies very small amplitude of strain.

The stress divided by strain was indicated by "modulus" and the stress divided by rate of strain was indicated in "viscosity". In dynamic experiment, the modulus and viscosity can be represented by complex number (or complex function) because stress and strain or rate of strain (all sinusoidal functions of time) are not necessarily in phase with one another. This is true for all viscoelastic materials and most of materials in nature (especially polymeric materials) are viscoelastic. The real or in-phase component of complex modulus is called "storage modulus", $G'$, and is a measure of energy stored and recovered per cycle of sinusoidal deformation (elastic component of material). The imaginary or 90° out of phase component of complex modulus is called "loss modulus", $G''$, and is a measure of the energy dissipated or lost as heat per cycle of sinusoidal deformation "viscous component of material).

The real or in-phase component of complex viscosity is called "dynamic viscosity" related to the loss modulus by the equation $n' = G''/w$, where w is frequency in rad/sec. The dynamic viscosity is a function of frequency in essentially the same way that the steady shear viscosity is a function of shear rate. Therefore, the rheological profile obtained by dynamic measurement is analogous to rheological profile obtained from steady measurement.

FIG. I illustrates the consistently lower complex modulus and complex viscosity over the entire frequency range with the B composition containing surfactant as compared to A composition without surfactant.

FIG. II compares the adhesion force of denture adhesive Compositions reported in Examples 1-5 where
■ represents 0.5% lecithin
+ represents 0.25% lecithin
* represents 0.125% lecithin
□ represents 0.0625% lecithin
⋈ represents 0.0% lecithin This Figure shows that in the formulation with white petrolatum and light mineral oil, as little as about 0.06% lecithin is capable of controlling the viscosity in the adhesive.

FIG. III compares the adhesion force of denture adhesive compositions in Examples 8, 11, 15 and 16 where ● represents 0.5% SANTONE 3-1-S
☐ represents 0.5% VERV Ca
✕ represents 0.5% GMS 90
◊ represents 0.5% CENTROLEX F
△ represents no surfactant This figure shows that while the adhesive force of the formulation with no surfactant is initially high, adhesion falls off rapidly and that, after 70 cycles, adhesion is less than those compositions containing surfactant.

In the above examples it is to be understood that other lecithins can be substituted for CENTROLEX-F e.g. OVATHIN or an individual lecithin such as phosphatidyl choline, to provide the viscosity limiting properties of high load denture adhesive formulations.

What is claimed is:

1. The process of applying to the biocontact surface of a denture an effective adhesive coating amount of an adhesive composition comprising a uniform dispersion of an innocuous adhesive polymeric resin in an oil base and a non-releasing amount of between 0.01 and 5 wt. % of a non-toxic, food grade surfactant selected from the group consisting of a lecithin, polyglycerol ester, alkali metal stearoyl lactate, a succinylated or ethoxylated mono- or di- glyceride and polyoxyethylene ether of a fatty acid ester of sorbitol anhydride, to provide a high polymer load gel adhesive.

2. The process of claim 1 wherein the adhesive coating is applied to the mating surface of the denture in a thickness of from about 0.5 to about 15 mils.

3. The process of claim 1 wherein said composition contains between about 0.05 and about 1 wt. % surfactant.

4. The process of claim 1 wherein the concentration of surfactant with respect to said polymer is between about 0.02 and about 10 wt. %.

5. The process of claim 4 wherein the concentration of surfactant with respect to said polymer is between about 0.1 and about 2 wt. %.

6. The process of increasing solids in a dental adhesive paste or gel formulation containing as solids a non-toxic polymeric resin which comprises adding to said formulation between 0.01 and 5 wt. % of a hydrolyzable, non-toxic surfactant of food grade quality.

7. The process of claim 6 wherein between about 0.05 and about 1 wt. % of said surfactant is added to said formulation.

8. The process of claim 6 wherein the concentration of said surfactant with respect to said resin is added in an amount of between about 0.02 and about 10 wt. %.

9. The process of claim 8 wherein the concentration of said surfactant with respect to said resin is added in an amount of between about 0.1 and about 2 wt. %.

10. The process of claim 6 wherein said surfactant is added to a suitable oil base for said resin at a temperature of from about 85° C. to about 200° C. to form a liquid composition and said resin is uniformly mixed with said surfactant/oil base liquid at between about 50° and about 180° C. to form a paste or gel containing up to 70% solids.

11. The denture adhesive product of claim 6.

* * * * *